US012778850B2

(12) United States Patent
Hines

(10) Patent No.: US 12,778,850 B2
(45) Date of Patent: Nov. 3, 2026

(54) SYSTEMS AND METHODS FOR DISPENSING MEDICATIONS USING AUTHENTICATION MECHANISMS

(71) Applicant: Dose Health, LLC, Golden Valley, MN (US)

(72) Inventor: Paul Hines, Golden Valley, MN (US)

(73) Assignee: Dose Health, LLC

( * ) Notice: Subject to any disclaimer, the term of this patent is extended or adjusted under 35 U.S.C. 154(b) by 115 days.

(21) Appl. No.: 18/848,009

(22) PCT Filed: Mar. 20, 2023

(86) PCT No.: PCT/US2023/064712
§ 371 (c)(1),
(2) Date: Sep. 17, 2024

(87) PCT Pub. No.: WO2023/178351
PCT Pub. Date: Sep. 21, 2023

(65) Prior Publication Data

US 2025/0195333 A1 Jun. 19, 2025

Related U.S. Application Data

(60) Provisional application No. 63/269,593, filed on Mar. 18, 2022.

(51) Int. Cl.

| | |
|---|---|
| ***A61J 7/00*** | (2006.01) |
| ***G06F 21/31*** | (2013.01) |
| ***G16H 20/13*** | (2018.01) |
| ***G16H 40/67*** | (2018.01) |

(52) U.S. Cl.
CPC ............ *A61J 7/0076* (2013.01); *G06F 21/31* (2013.01); *G16H 20/13* (2018.01); *G16H 40/67* (2018.01)

(58) Field of Classification Search
CPC ...... A61J 7/0076; A61J 7/0084; A61J 7/0445; A61J 7/0481; G06F 21/31; G16H 20/13; G16H 40/67; G16H 40/63; G07F 17/0092
See application file for complete search history.

(56) References Cited

U.S. PATENT DOCUMENTS

| | | | | |
|---|---|---|---|---|
| 4,572,403 | A * | 2/1986 | Benaroya .................. | A61J 7/04 221/76 |
| 6,234,343 | B1 * | 5/2001 | Papp .................. | G07F 17/0092 221/7 |
| 6,439,422 | B1 | 8/2002 | Papp | |

(Continued)

OTHER PUBLICATIONS

International Search Report and Written Opinion, Application No. PCT/US2023/064712, mailed Jul. 17, 2023, 12 pages.

*Primary Examiner* — Michael Collins
(74) *Attorney, Agent, or Firm* — Merchant & Gould P.C.

(57) ABSTRACT

A system for dispensing medication to ensure the correct medication is dispensed to the correct patient at the correct time. The system includes a base configured to mechanically engage with a removable carousel comprising a plurality of compartments. The system also includes authentication features or devices that store information relating to the mode the device operates in and patient information. The authentication feature or device can be mechanical or electronic and ensure that medication is dispensed properly. The system can include multiple devices for dispensing medication that communicate with each other and a processor.

14 Claims, 12 Drawing Sheets

(56) References Cited

U.S. PATENT DOCUMENTS

| | | | | |
|---|---|---|---|---|
| 6,651,840 | B1 * | 11/2003 | Van Dullemen | B65D 83/0463 221/88 |
| 7,108,153 | B2 * | 9/2006 | Wood | A61J 7/0076 221/152 |
| 7,661,532 | B2 | 2/2010 | Conley | |
| 7,735,684 | B2 | 6/2010 | Coe | |
| 9,965,594 | B2 | 5/2018 | Portney | |
| 11,116,698 | B2 * | 9/2021 | Brady | G16H 20/13 |
| 11,116,699 | B2 | 9/2021 | Hines | |
| 11,432,999 | B2 | 9/2022 | Hines | |
| 2003/0231119 | A1 * | 12/2003 | Chiavetta | A61J 7/0084 340/870.07 |
| 2021/0100722 | A1 | 4/2021 | Hines | |
| 2021/0401673 | A1 | 12/2021 | Feng | |
| 2023/0338240 | A1 * | 10/2023 | Willett | G16H 20/13 |

* cited by examiner

SYSTEMS AND METHODS FOR DISPENSING MEDICATIONS USING AUTHENTICATION MECHANISMS

CROSS-REFERENCE TO RELATED APPLICATIONS

This application is being filed on Mar. 20, 2023, as a PCT International application and claims the benefit of and priority to U.S. Provisional Patent Application Ser. No. 63/269,593, filed on Mar. 18, 2022, the entirety of which is incorporated herein by reference.

BACKGROUND

Many people across the world rely on medications to regulate and treat health conditions. Pill organization systems are often used to organize medications by pills to be taken on certain days and even at certain times of day. The systems commercially available typically include 7-28 compartments, though containers with fewer and greater compartments are available.

In a typical pill organization system, medications are pre-loaded into a container that holds medication sufficient for a particular period of time (e.g., one week) and may include multiple compartments per day (e.g., morning and night for a single day). Such organizing systems are beneficial for consumers to track if they have taken their necessary medication for the day. However, these systems require the user to regularly monitor their own adherence to a medication regimen without monitoring or intervention by a healthcare provider, which can be challenging, especially for people with limited capacity or those taking numerous medications at a time.

Additionally, typical pill organization systems require physical opening and closing of the systems and medication containers, which requires manual dexterity to manipulate. This is challenging for some people who have limited mobility, strength, or dexterity, which can lead to lack of adherence and spilling and improperly mixing medications.

To address some of these concerns, automatic medication dispensers have recently become commercially available that automatically dispense medications at a certain time and date. However, many of these systems are bulky, not user friendly, and require constant connection to a power source. This leads to lack of medication adherence due to the complexity of the systems and the lack of portability for travel. The ability to access medications during travel is especially important for patients that may require frequent trips to healthcare appointments or other care facilities that may be far from the patient's home.

SUMMARY

A variety of additional inventive aspects will be set forth in the description that follows. The inventive aspects can relate to individual features and to combinations of features. It is to be understood that both the forgoing general description and the following detailed description are exemplary and explanatory only and are not restrictive of the broad inventive concepts upon which the embodiments disclosed herein are based.

According to a first aspect, a system for dispensing medication includes a base having a locking authentication feature and a motor: a removable carousel comprising a plurality of compartments and a corresponding locking authentication feature, wherein the removable carousel is configured to mechanically engage with the motor when the locking authentication features of the base and the removable carousel match one another.

According to another aspect, a system for dispensing medication includes a base: a removable carousel comprising a plurality of compartments and an electronic authentication device: wherein the removable carousel is configured to mechanically engage with the base; and a processor configured to operate the system based upon information stored in the electronic authentication device.

According to another aspect, a medication dispensing system includes a first device. The first device includes a base and a first removable carousel comprising a plurality of compartments and a first authentication device, the first removable carousel configured to mechanically engage with the first base, a processor configured to operate the system based upon information stored in the first electronic authentication device, and a first screen. The second device includes a second base, a second removable carousel comprising a plurality of compartments, the second removable carousel configured to engage with the second base.

BRIEF DESCRIPTION OF THE DRAWINGS

The accompanying drawings, which are incorporated in and constitute a part of the description, illustrate several aspects of the present disclosure. A brief description of the drawings is as follows.

DETAILED DESCRIPTION

Reference will now be made in detail to exemplary aspects of the present disclosure that are illustrated in the accompanying drawings. Wherever possible, the same reference numbers will be used throughout the drawings to refer to the same or like parts.

Figure 1:
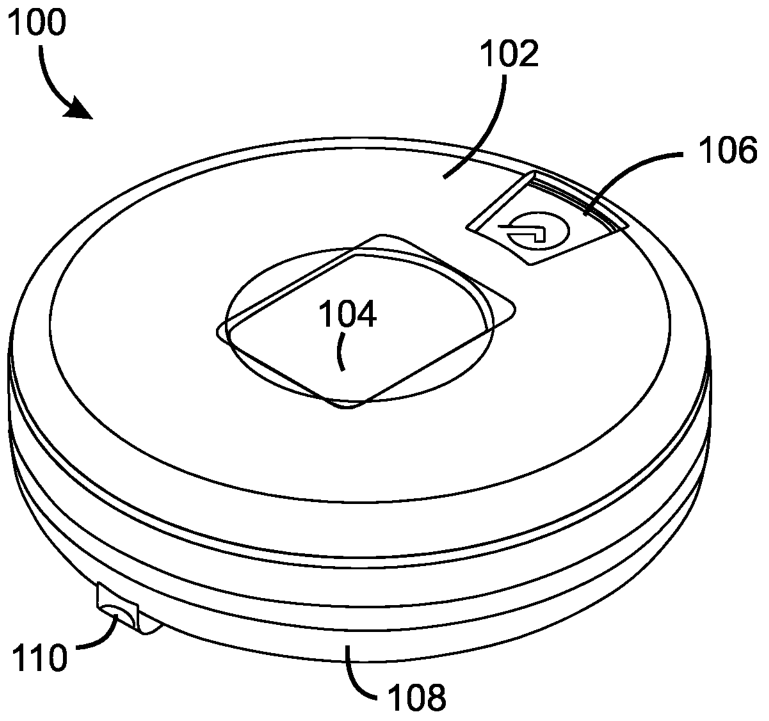
FIG. 1 depicts a perspective view of a medication dispensing system according to an embodiment.

The disclosure relates to systems and methods for using automatic pill dispensing systems with interchangeable carousels and interconnected devices. FIG. 1 depicts a medication dispensing system 100, according to an example of the disclosure. As shown in FIG. 1, medication dispensing system 100 includes a lid 102, a screen 104, a zero-position indicator 106, a base 108, and a charging port 110. Further details regarding aspects of medication dispensing system 100 can be found in U.S. Pat. No. 11,432,999, the entirety of which is incorporated herein by reference. Medication dispensing system 100 is shown with a circle shape in FIGS. 1-3, however other parallelogram shapes are contemplated such as squares, rectangles, triangles, trapezoids, pentagons, hexagons, etc.

Figure 2:
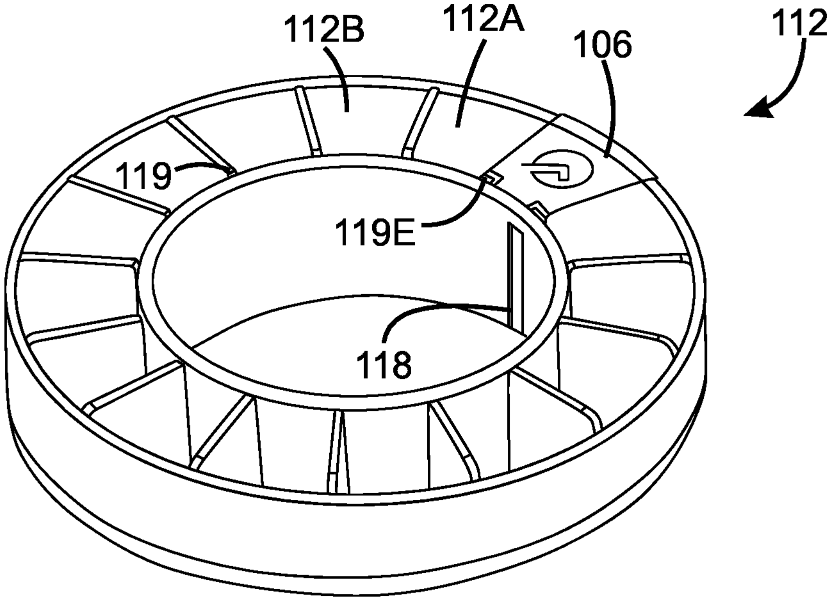
FIG. 2 is a perspective view of a carousel for use with the medication dispensing system of FIG. 1, according to an embodiment.

According to an example of the disclosure, medication dispensing system 100 includes a removable carousel, or tray, 112, as shown in FIG. 2. Removable carousel 112 includes a plurality of compartments, or bins, 112A, 112B, etc. for holding medications. In some examples, removable carousel 112 has 7 compartments, 14 compartments, or 21 compartments. In other examples, removable carousel 112 may include a number of compartments that is a multiple of 7 to be compatible with a weekly medication schedule, such as 28 compartments. In other examples, different medication schedules may be based on other periods, such that removable carousel 112 may include any number of compartments from 1-40, i.e., 1 compartment, 2 compartment, 3 compartments, 5 compartments, 15 compartments, 20 compartments, 40 compartments, and all integers in between.

Using more than 40 compartments in the embodiment shown in FIG. 2 could lead to individual compartments that are too small to hold most medications. Additionally, depending on the dispensing schedule, using a device having more than 40 compartments could result in medications that are stored in the device past their shelf life. However, larger devices, devices that dispense medications with long shelf lives, or devices that dispense only a small amount of material may include even higher numbers of compartments.

Removable carousels 112 with different numbers of compartments may be used with the same medication dispensing system 100. Removable carousel 112 may also include a slot 118 configured to engage with a tooth (as shown in FIG. 1G of U.S. Pat. No. 11,432,999) associated with a motor 114 (shown in FIG. 3). Removable carousel 112 may also include gaps 119 between the walls of each compartment and the center of the removable carousel 112, and gap ends 119E on the zero-position indicator 106, the details of which are discussed in U.S. Pat. No. 11,432,999.

Figure 3A:
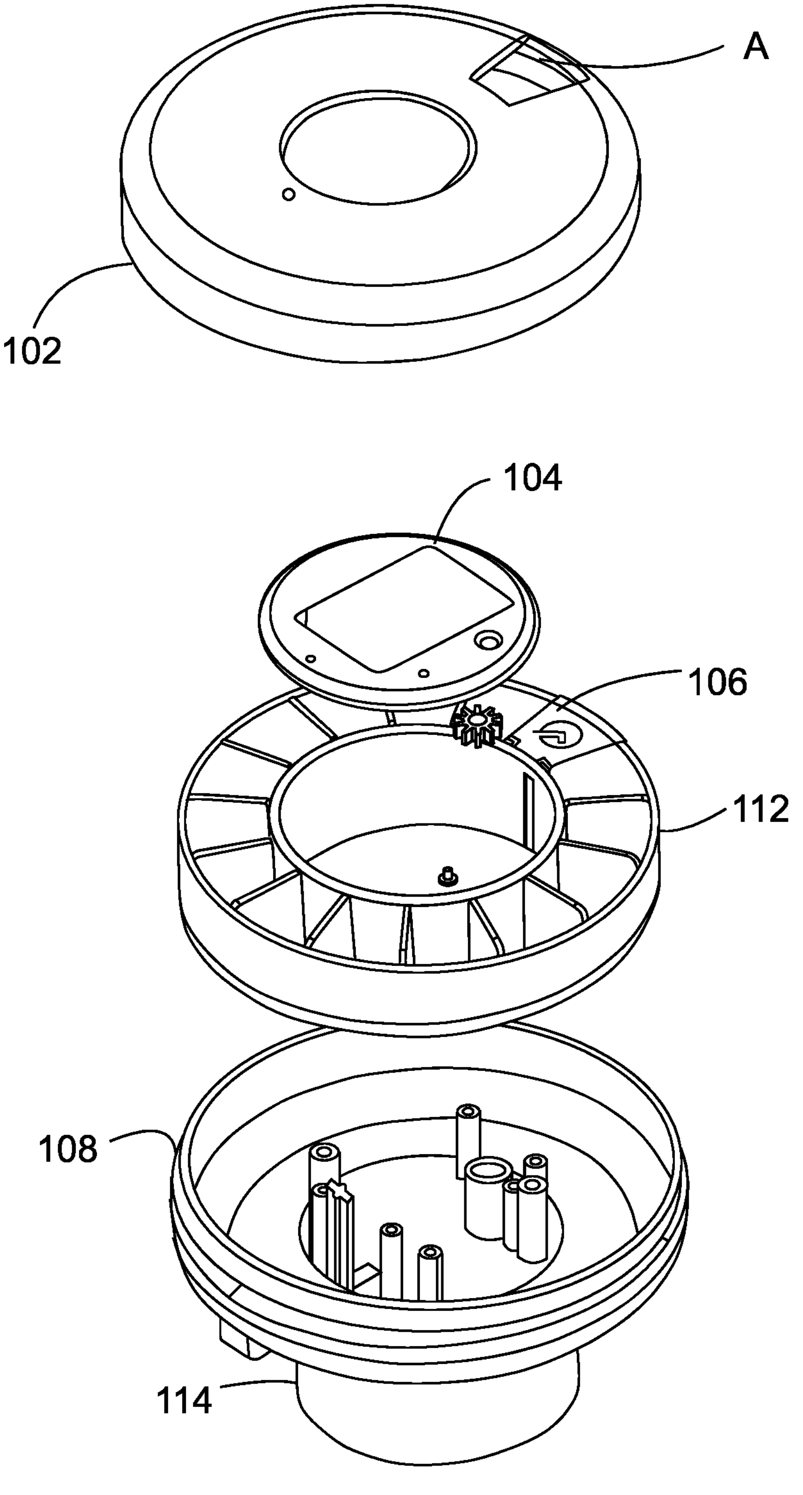
FIG. 3A is an exploded view of the medication dispensing system of FIG. 1.

FIG. 3A shows an example exploded view of a removable carousel 112 that engages with base 108, with screen 104 and lid 102 placed on top of the removable carousel 112. Lid 102 includes an aperture A. Other assembly configurations are contemplated, such as a screen 104 integrated into the lid 102, the removable carousel 112, or the base 108.

Medication dispensing systems 100 may automatically dispense medications on a predetermined schedule. For example, a patient that takes one medication twice per day may have a system 100 with 14 compartments. System 100 may dispense one pill in the morning and one pill in the evening for the duration of one week, with each pill in a separate compartment. Or, for example, if a patient takes four medications, each twice per day, each compartment of a removable carousel 112 with 14 compartments would have 4 pills. In the morning, system 100 would dispense 4 pills from one compartment and dispense 4 pills from another compartment in the evening, and then repeat for 7 days until all 14 compartments are empty.

It has been found that even when the aperture A in the lid 102 has been sized to correspond to a 14-compartment removable carousel 112, that aperture A provides sufficient egress for pills dispensed from a 7-compartment tray. The aperture A sized for a 14-compartment removable carousel 112 would only expose about half of a compartment of a 7-compartment removable carousel. However, it has been found that this is sufficient to dispense medications contained within the compartment successfully.

However, if a medication dispensing system 100 was programmed to dispense medication from a 7-compartment removable carousel 112 but a user had mistakenly installed a 14-compartment removable carousel 112 into the system 100, system 100 may not dispense the correct amount of medication at the correct time according to the user's medication regimen. For example, the medication dispensing system 100 may be programmed to expose compartments at only seven positions of the removable carousel 112, such that only half of the proper doses of medication are dispensed.

On the other hand, if a 14-compartment removable carousel 112 is installed but the medication dispensing system 100 should receive a 7-compartment removable carousel, then a larger compartment could be exposed twice at different times on the dispensing schedule (first on one half, then the other) such that no medication is dispensed at some of the scheduled medication dispensing times.

Additionally, in a setting such as nursing homes or care facilities, many people may use separate medication dispensing systems 100. Each person has a specific medication regimen with different medications that must be taken on different schedules. If a medication is given to the wrong person, that person can suffer from severe health repercussions, or even death. Thus, it is important to ensure that a medication dispensing system 100 dispenses the correct medication, at the correct time, to the correct user.

To ensure that medication dispensing system 100 dispenses the correct medication, at the correct time, to the correct user, the system 100 may include authentication mechanisms. In some examples, the authentication mechanisms are mechanical. In some examples, the authentication mechanisms are local electronic. In some examples, the authentication mechanisms require authentication from a remote, networked device. In some examples, the system 100 uses some combination of mechanical, electronic, and networked authentication mechanisms.

In systems 100 with a mechanical authentication mechanism, a removable carousel 112 is configured to engage with the base 108. Removable carousel 112 may engage with the base 108 using a locking authentication feature. The locking authentication feature can include a lock-and key fit, a snap-fit fastener, magnets, screw-in mechanism, or any other suitable means of mechanical connection known in the art. The base 108 has a locking authentication feature, and the removable carousel 112 has a corresponding locking authentication feature. The removable carousel 112 is configured to mechanically engage with the base 108 when the locking authentication feature of the base 108 and the corresponding locking authentication feature of the removable carousel 112 match one another. For example, the locking authentication feature of base 108 may include a round peg extending upward from an interior of the base 108. Removable carousel 112 may include a corresponding locking authentication feature that is a round hole on the underside of removable carousel 112 that matches the round peg on base 108. When the locking authentication features match, the base 108 and the removable carousel 112 will mechanically engage with one another.

In some examples, removable carousels 112 with a different number of the plurality of components will have a different locking authentication feature. For example, a 7-compartment removable carousel 112 may have a round hole that corresponds to a base 108 with a round peg in a medication dispensing system 100 programmed to use a 7-compartment removable carousel 112: a 14-compartment removable carousel 112 may have a square hole that corresponds to a base 108 with a square peg in a medication dispensing system 100 programmed to use a 14-compartment removable carousel 112; a 21-compartment removable carousel 112 may have a triangle hole that corresponds to a base 108 with a triangle peg in a medication dispensing system 100 programmed to use a 21-compartment removable carousel 112, etc. Other shapes and configurations of mechanical locking authentication features are contemplated, such as a lock-and key fit, a snap-fit fastener, magnets, screw-in mechanism, or any other suitable means of mechanical connection known in the art. A removable carousel 112 with any number of compartments may be used with any type of locking authentication feature described above.

Figure 3B:
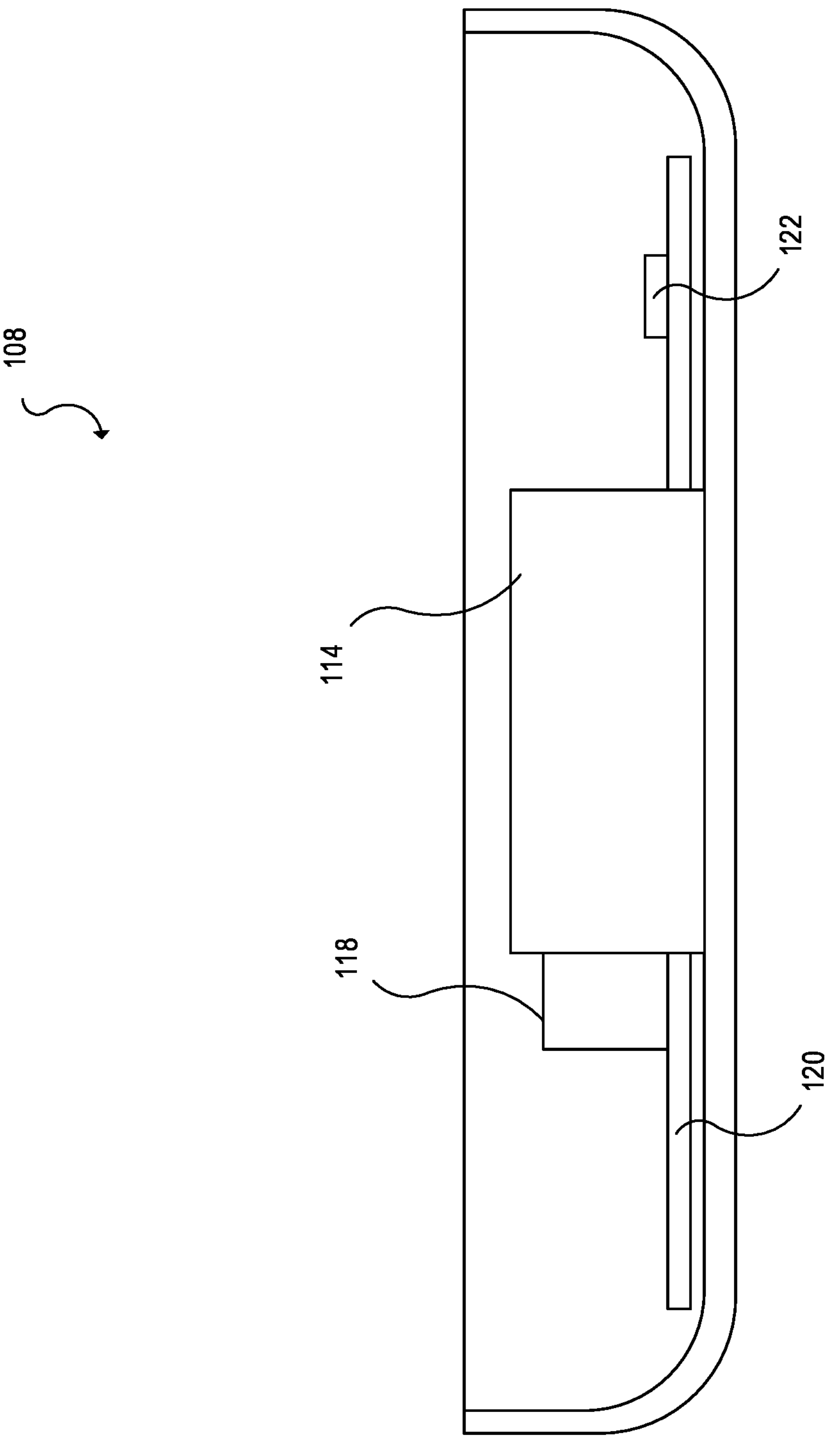
FIG. 3B is a cross-sectional view of a base of a medication dispensing system according to an embodiment.

FIG. 3B shows a cross-sectional view of a base that includes such mechanical locking mechanisms according to one embodiment. As shown in FIG. 3B, the base 108 includes similar components to those described above, including a motor 114 and a fin 118 that can be rotated by the motor 114 to dispense medications from various bins within a carousel (not shown in FIG. 3B).

In addition, FIG. 3B shows a receiver 120 that is configured to receive the bottom of the carousel. On the receiver 120 is arranged a feature 122 that interlocks with the bottom of an appropriate carousel. The size, shape, and thickness of the feature 122 correspond to a particular carousel or type of carousel.

For example, the size, shape, and thickness of the feature 112 can correspond to a carousel that has 14 trays. A different feature 122 on a different receiver 120 could correspond to carousels with 7 trays. In still further embodiments, a receiver could have one or more features 112 that are custom-designed for a particular patient or type of medication.

The number of options for features 122 are varied. In general, the number, size, height, and shape of the features 122 on any given receiver 120 are selected so that they prevent the lid 102 from being closed when an incompatible carousel 112 is inserted into the device 100. There may also be, for example, magnetic or electronic interlocking features arranged on the mechanical shape that makes up the feature 112. Such features could detect correct or compatible adjacent features in a compatible carousel, such as the features described below with respect to FIGS. 4A-4F.

Figure 4A:
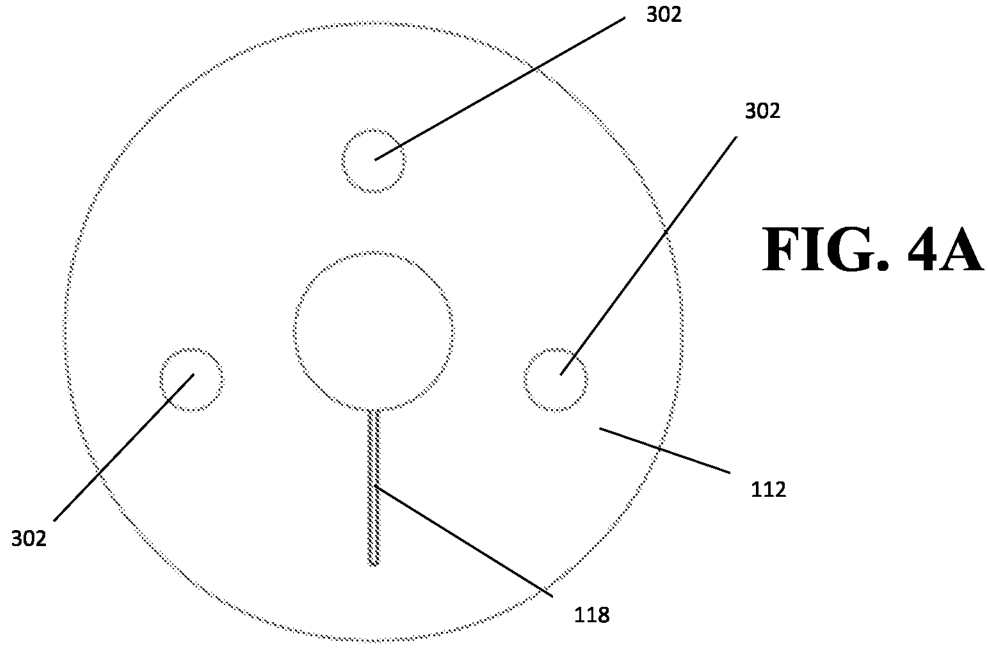
FIGS. 4A-4F are bottom plan views of carousels incorporating mechanical and electrical locking authentication features according to various embodiments.
Figure 4B:
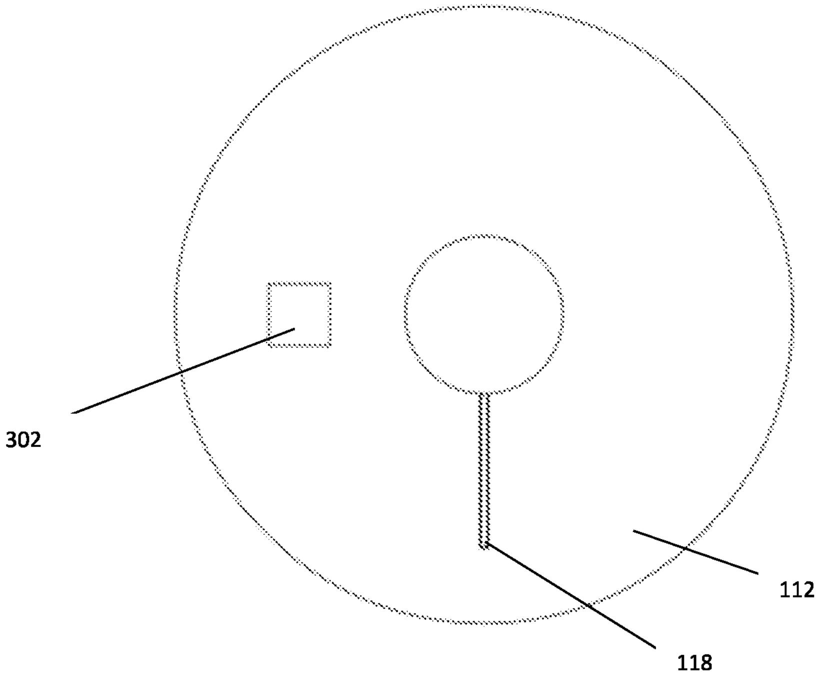

FIGS. 4A-4F show example corresponding locking authentication features 302 on the bottom of removable carousel 112. The bottom of removable carousel 112 may include any number of corresponding locking authentication features 302. FIG. 4A shows an example with three circular corresponding locking authentication features 302 on the bottom of the removable carousel 112. FIG. 4B shows an example of one square corresponding locking authentication feature 302. As described above, the corresponding locking authentication features 302 can be holes on the bottom of the removable carousel 112 that correspond to pegs used as features 122 of the same shape (FIG. 3B).

Figure 4C:
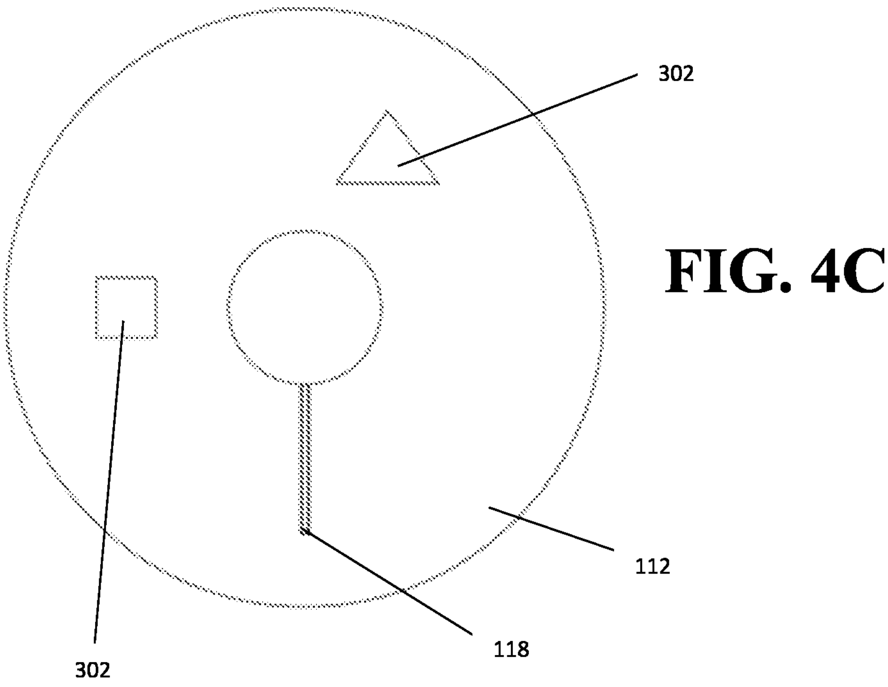
Figure 4D:
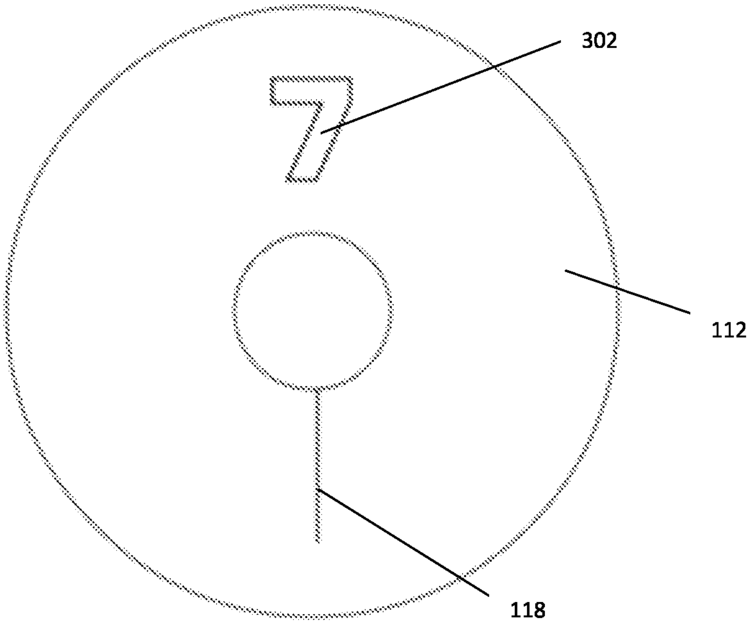

FIG. 4C shows an example with one triangle and one square corresponding locking authentication features 302. A base corresponding to the removable carousel 112 with these corresponding locking authentication features 302 would have a triangle shaped peg and a square shaped peg corresponding to the size and location of the corresponding locking authentication features 302. In some examples, the corresponding locking authentication features may represent the number of the plurality of compartments in the removable carousel 112. For examples. FIG. 4D shows a removable carousel 112 with a corresponding locking authentication feature 302 that is in the shape of the number 7, which would correspond to a removable carousel 112 with 7 compartments. A similar removable carousel 112 could have a corresponding locking authentication feature 302 in the shape of the number 14, which would correspond to a removable carousel 112 with 14 compartments. The corresponding locking authentication feature 302 can be in the shape of any number of possible compartments contemplated in this disclosure, such as numbers that are multiples of 7 and integers between 1 and 40. In some examples, the corresponding locking authentication features 302 can be any three-dimensional shape, such as the ridges on a key. Corresponding locking authentication features 302 that are more complex may be desirable in settings where there are numerous systems 100, such as in nursing homes or care facilities, such as to better differentiate between removable carousels 112 and bases 108 associated with different people.

In some examples, the locking authentication feature on the receive 120 (FIG. 3B) has a depth sufficient to engage with the corresponding locking authentication feature 302 on the removable carousel 112. However, the depth of the locking authentication feature 122 on receiver 120 is not so deep as to interfere with the lid 102 fitting on the system 100. The locking authentication feature on the base has a limited depth so as not to interfere with pills fitting in the compartments of the removable carousel 112. In some examples, the locking authentication feature on the base has a depth of less than 2 centimeters, less than 1 centimeter, less than 0.75 centimes, less than 0.5 centimeters, or less than 0.25 centimeters so are not to interfere with the lid 102 mechanically engaging with the base 108 when the removable carousel 112 is inside, and so as not to interfere with the space in any compartment in the removable carousel 112.

In some examples, the locking authentication feature and the corresponding locking authentication feature are located elsewhere on the system 100. For example, the slot 118 may include protrusions or "teeth" that can act as a locking authentication feature and a corresponding locking authentication feature. In some examples the vertical wall on the inner ring of the removable carousel 112 where the slot 118 is located can include the locking authentication feature and/or the corresponding locking authentication feature to connect to the base 108. In some examples, the lid 102 may also include the locking authentication feature and the corresponding locking authentication feature.

If the locking authentication feature on the base 108 and the locking authentication feature on the removable carousel 112 do not match, the base 108 and the removable carousel 112 will not mechanically engage with each other. This prevents a user from using a base 108 with the wrong removable carousel 112 that may: include the wrong medication, be associated with the wrong patient, or have a number of the plurality of compartments that does not correspond to the programming of medication dispensing system 100.

If the locking authentication feature 122 on the receiver 120 and the corresponding locking authentication feature on the removable carousel 112 match, the receiver 120 and the removable carousel 112 will mechanically engage and be rotated together by the motor 114. A user may then install the screen 104 and the lid 102. The lid 102 is configured to mechanically engage with the base 108, and the lid defines aperture A. When assembled, the removable carousel is arranged between the base 108 and the lid 102 when the base 108 and the lid 102 are mechanically engaged.

Once the base 108 and the removable carousel 112 are mechanically engaged, the medication dispensing system 100 is ready for use (discussed below). The medication dispensing system 100 further comprises a processor 702 (shown and described in FIG. 8) configured to operate the system 100 based upon a match between the locking authentication feature of the base 108 and the corresponding locking authentication feature of the removable carousel 112. The processor 702 may select an operating mode to dispense medication. The operating mode can be selected using parameters such as the number of the plurality of compartments, the frequency of dispensing the medication, and patient identifying information.

In some examples, system 100 uses an electronic authentication device to ensure the correct user is taking the correct medication at the correct time. The electronic authentication device may include an RFID tag, an ultrawide band (UWB) device, a Bluetooth device, or NFC tag. In some examples, the system 100 comprises a base 108 and a removable carousel 112 comprising a plurality of compartments and an electronic authentication device, wherein the removable carousel 112 is configured to mechanically engage with the base 108. The electronic authentication device may be placed on a surface of the removable carousel 112, such as on the bottom, on the side, or in the compartments. In some examples, the electronic authentication device is integrated or embedded into the material of the removable carousel 112.

Figure 4E:
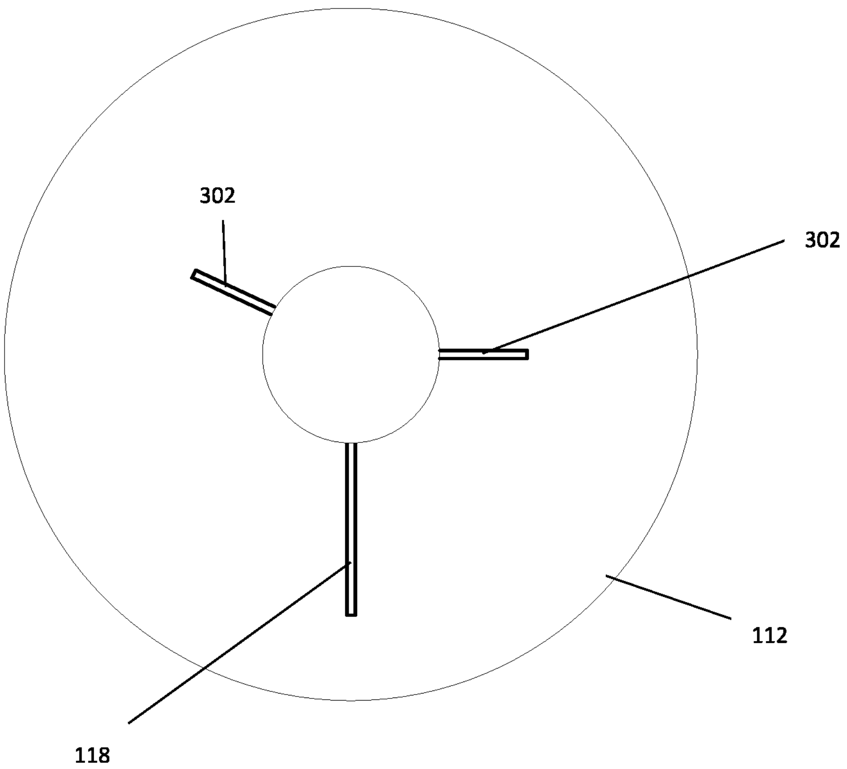

FIG. 4E shows a different type of mechanical engagement feature that can be used in some embodiments. In lieu of features 122 as shown in FIG. 3B that extend from a tray, the embodiment shown in FIG. 4E includes a plurality of slots 302 in addition to the slot corresponding to the driving fin 118. In the embodiment shown in FIG. 4E, the motor (rather than the carousel) can have engagement features attached to it. As will be appreciated from FIG. 4E, a motor 114 can have a plurality of fins extending therefrom, and such fins can have a key-like arrangement to fit with corresponding carousels. The length, radial positioning, and thickness of fins on a motor 114 can be selected to correspond to only some types of carousels, and prevent carousels from being loaded into incorrect devices 100 based on the fins of the motor 114.

Figure 4F:
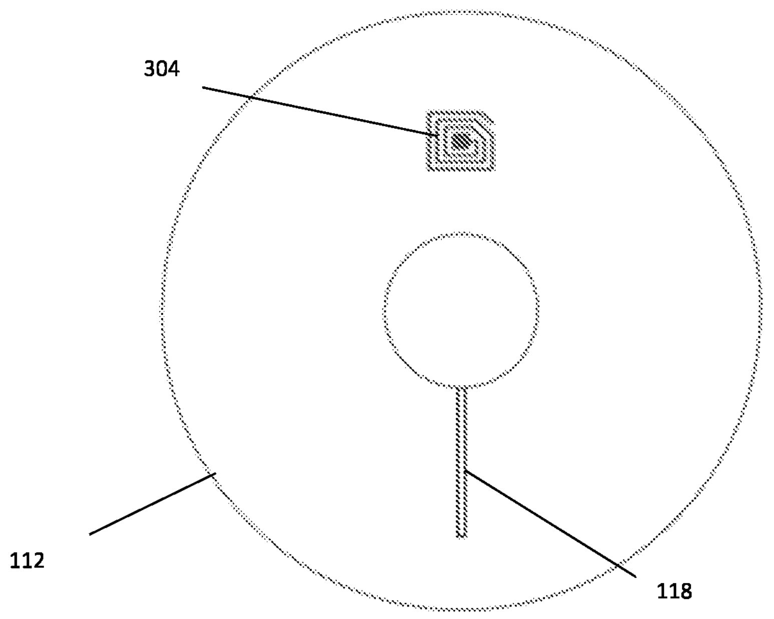

FIG. 4F shows an example electronic authentication device 304. The electronic authentication device 304 may be disposed on the bottom surface of the removable carousel 112 and can interact with an electronic reader on the base 108 or on a corresponding receiver (120, FIG. 3B). The electronic authentication device 304 can be located on any part of the removable carousel 112 such as on the bottom, on the sides, in a compartment, or embedded into the material of the removable carousel 112.

Electronic authentication device 304 can be an RFID chip, an NFC chip, or any of a variety of other powered or unpowered wireless communication components. In some embodiments, electronical authentication device 304 can also be wired, rather than wireless. For example, if a carousel connects mechanically such that the electronic authentication device 304 is in direct contact with the motor 114 or receiver 120, then the electronic authentication device 304 can send or receive power and information directly through that connection.

Pairing using an electronic authentication device 304 has some advantages to mechanical pairing. For example, electronic pairing does not necessarily require any mechanical incursion by the pairing device into the space that could otherwise be taken by the pill dispenser. That is, an RFID chip or the like can be implanted into the side of the motor 114 or into the receiver 120 to communicate with a corresponding chip in the carousel, and such RFID chips would not need to protrude physically into the form factor of either component.

Furthermore, electronic pairing can be more sophisticated than a mechanical pairing, which is generally limited to devices that are either compatible or incompatible. An electronic pairing could, for example, rely upon information that is pre-stored into an electronic chip that could identify the patient, the medications in the carousel, expiration dates, refill schedules, or other such information. In the scenario where multiple devices are used in a single residence, the RFID chip can include sufficient information for the device 100 to update its settings automatically upon reading the chip in a received carousel. The information stored in the electronic pairing element (e.g., electronic authentication device 304) can include not only authentication, but also setup information that instructs the device 100 to change its settings from 14-component to 7-component (see FIG. 5) or make other similar adjustments.

Electronic pairing or settings updates can be made using an electronic authentication device 304 alone, as shown in FIG. 4F. However, it should be understood that there can be combinations of mechanical and electrical pairing. For example, the electronic authentication device 304 could be in a carousel along with any of the mechanical authentication systems of FIGS. 4A-4E, among others.

The system 100 also can include a processor 702 (shown in FIG. 8) configured to operate the system 100 based upon information stored in the electronic authentication device. The type of information that can be stored in the electronic authentication device includes patient identifying information such as name, date of birth, Medicaid or Medicare number, or other information traditionally known at Protected Health Information (PHI), and the number of the plurality of compartments in a removable carousel 112, which is collectively referred to as information.

The processor 702 of the medication dispensing device 100 also stores information such as patient identifying information such as name, date of birth, Medicaid or Medicare number, or other information traditionally known at Protected Health Information (PHI). The processor 702 can store information such as patient identifying information, the number of the plurality of compartments in a carousel 112, which is collectively referred to as information. The processor 702 in a medication dispensing system 100 with a mechanical authentication mechanism or an electronics authentication device can store this information.

When the base 108 and the removable carousel 112 are mechanically engaged, the electronic authentication device communicates with the processor 702 in the medication dispensing system 100. The processor 702 compares the information stored in the processor 702 and the information stored in the electronic authentication device to see if the information matches. As discussed above, the processor 702 can store information about the number of the plurality of compartments that is associated with an operating mode (e.g., if the processor 702 is programmed to use a 7-compartment removable carousel 112, the processor 702 enables the 7-compartment operating mode). The electronic authentication device can store similar information associated with an operating mode (e.g., the electronic authentication device is connected to a removable carousel 112 with a number of plurality of compartments, and the electronic authentication devices stores that number). If the information in the electronic authentication device of the number of the plurality of compartments does not match the operating mode selected by the process, the system 100 will not dispense medication. This indicates that there is a mismatch between the operating mode and the number of the plurality of compartments. For example, this could mean that a 7-compartment removable carousel 112 has been placed in the base 108 when the operating mode is a 14-compartment operating mode.

As discussed above, the processor 702 and the electronic authentication device can also store patient identifying information such as name, date of birth, Medicaid or Medicare number, or other information traditionally known at Protected Health Information (PHI). If the patient identifying information in the electronic authentication device does not match the patient identifying information in the processor 702, the system 100 will not dispense medication. If any of the information in the electronic authentication device does not match the information stored by the processor 702, the processor 702 will display an error message on the screen 104 of the system 100. This can include a mismatch between patient identifying information or the number of the plurality of compartments. In some examples, if there is a mismatch, the processor 702 will send a message to a healthcare provider that there is a mismatch between the information stored in the electronic authentication device and the information stored in the processor 702.

Figure 5:
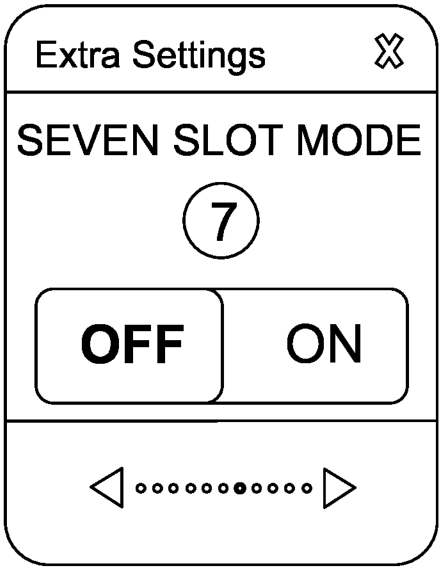
FIG. 5 is a user interface illustrating an example 7-compartment mode for use with the medication dispensing system of FIG. 1, according to an embodiment.

According to examples of the disclosure, when medication dispensing system 100 is in use, the screen 104 may display a user interface with numerous features a user can select. In some examples, the screen may present a user with an option to select how many compartments are in the removable carousel 112 to be used with medication dispensing system 100. FIG. 5 depicts an example screen where a user can turn a 7-compartment (or 7-slot) mode on, meaning that a removable carousel 112 with seven compartments will be used with medication dispensing system 100. The screen 104 may also include a similar user interface with a 14-compartment mode, meaning that a removable carousel 112 with 14 compartments will be used with medication dispensing system 100, or a 21-compartment mode, meaning that a removable carousel 112 with 21 compartments will be used with medication dispensing system 100, and so forth. A single medication dispensing system 100 may include options for a 7-compartment mode, a 14-compartment mode, a 21-compartment mode, and a 28-compartment mode, and combinations thereof. In some examples, a medication dispensing system 100 may include operating modes for any number of compartments 1 to 40 (e.g., a 1-compartment operating mode, a 2-compartment operating mode, a 3-compartment operating mode, a 5-compartment operating mode, a 15-compartment operating mode, a 40-compartment operating mode).

In some examples, the processor 702 is configured to automatically switch operating modes when a removable carousel 112 with an electronic authentication device storing information is mechanically engaged in the base 108. For example, if a user is setting up a medication dispensing system for the first time, it may be desired that when the base 108 and the removable carousel 112 are mechanically engaged, the information stored in the electronic authentication device directs the processor 702 to select an operating mode corresponding to the information stored in the electronic authentication device. For example, if a user places a 7-compartment removable carousel 112 into the base 108, the electronic authentication device may direct the processor 702 to enable 7-compartment mode. This may also be useful if a user experiences a change in their medication regimen, such as a medication quantity and/or frequency increase or decrease that requires a different removable carousel 112 to be used. Placing a new removable carousel 112 with an electronic authentication device into the base 108 can direct the processor 702 change the operating mode.

As with the medication dispensing system 100 with mechanical locking authentication features, a medication dispensing system 100 with an electronic authentication device may include a lid 102. The lid 102 is configured to mechanically engage with the base 108, and the lid defines aperture A. When assembled, the removable carousel is arranged between the base 108 and the lid 102 when the base 108 and the lid 102 are mechanically engaged.

In some examples, a medication dispensing system 100 may include both mechanical locking authentication features and electronic authentication devices. For example, a base 108 and a removable carousel 112 may include mechanical locking authentication features such as a lock-and-key fit with a peg on the base 108 and a hole on the removable carousel 112 to mechanically engage the base 108 and the removable carousel 112. Additionally, the removable carousel 112 may also include an electronic authentication device that communicates with the processor 702 information. All of the features described above for the mechanical locking authentication features and the electronic authentication devices may apply to a system 100 using both authentication mechanisms.

Figure 6A:
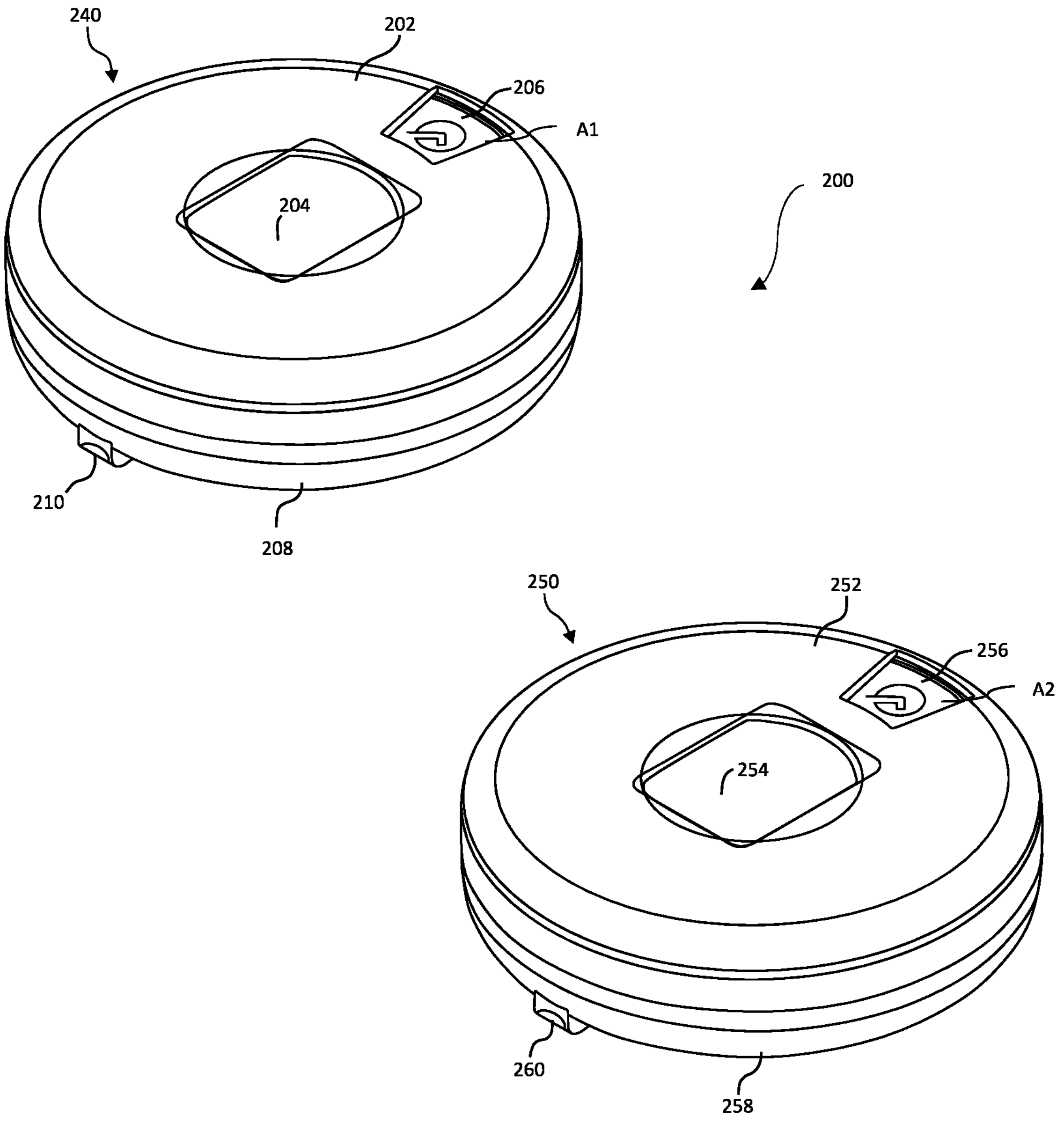
FIG. 6A is a perspective view of a system with two devices for a medication dispensing system, according to an embodiment.
Figure 6B:
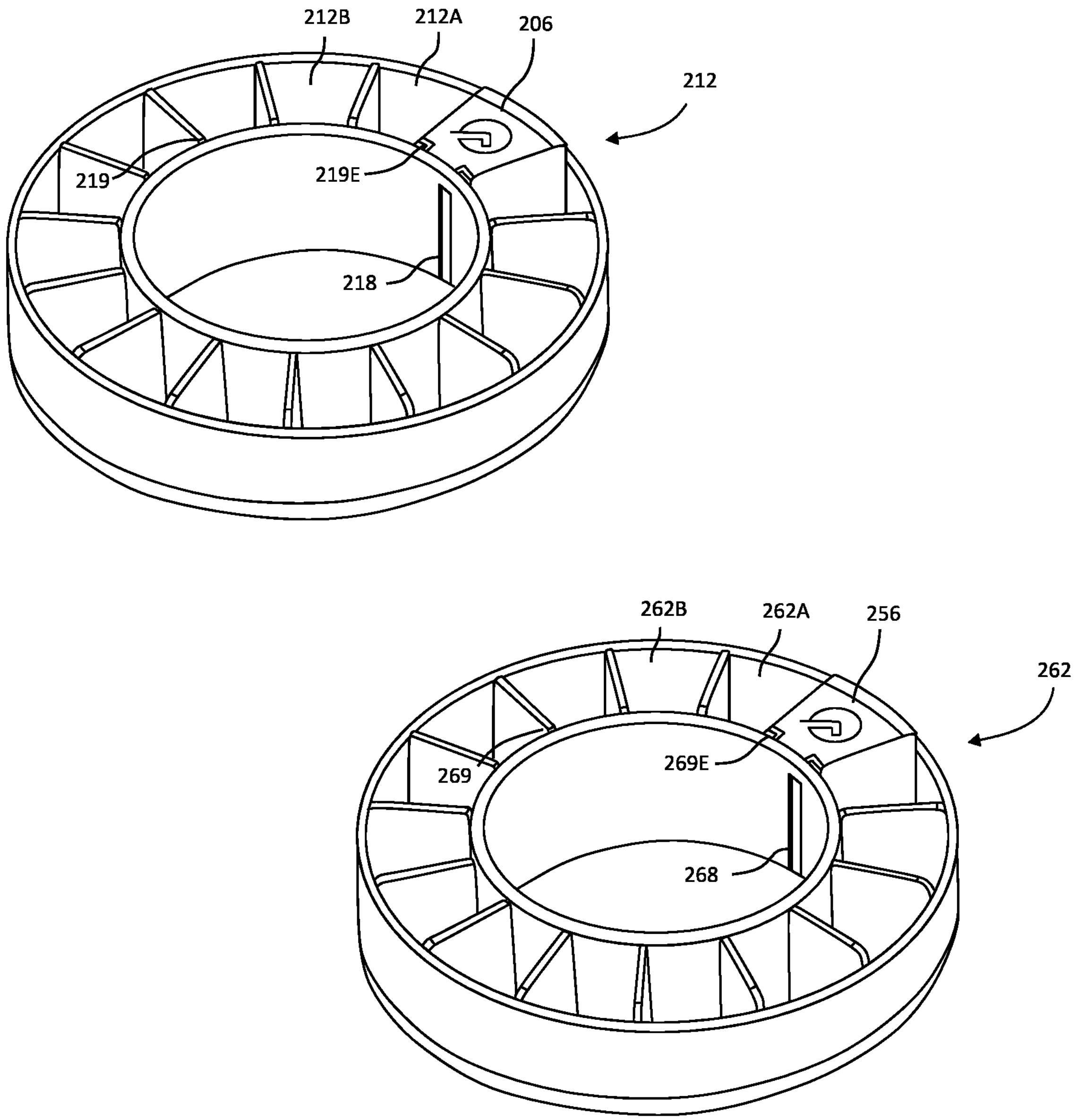
FIG. 6B is perspective view of removable carousels to be used with the system of FIG. 6A.

In some examples of the disclosure, there is a medication dispensing system 200 with two or more devices, shown in FIGS. 6A and 6B. In some examples, the system 200 includes two devices, a first device 240 and a second device 250. In some examples, there are an infinite number of devices that can be used in a single system 200 (e.g., 4 devices, 12 devices, 34 devices, 87 devices). Each device in a system 200 functions similarly to the system 100, and all the features described above for system 100 apply to each device in system 200. Therefore, a single system 100 in FIGS. 1-3 and a first device 240 and a second device 250 in FIGS. 6A and 6B may have the same features as one another.

In some examples, medication dispensing system 200 comprises a first device 240 that has a first base 208 and a first removable carousel 212 (shown in FIG. 6B). The first device 240 also includes a first screen 204, a first charging port 210, a first lid 202, and a first zero position indicator 206. Like with system 100 described above, the first removable carousel 212 comprises a plurality of compartments and is configured to mechanically engage with the first base 208. A user may assemble first device 240 by placing first removable carousel 212 into the first base 208, and then install the first screen 204 and the first lid 202. The first lid 202 is configured to mechanically engage with the first base 208, and the first lid 202 defines first aperture A1. When assembled, the first removable carousel 212 is arranged between the first base 208 and the first lid 202 when the first base 208 and the first lid 202 are mechanically engaged. The first device 240 also includes a first authentication device and a processor 702 configured to operate the system 200 based upon information stored in the first electronic authentication device.

The first removable carousel 212 comprises a plurality of compartments 212A, 212B, etc. First removable carousel 212 may also include first gaps 219 between the walls of each compartment and the center of the first removable carousel 212, and first gap ends 219E on the zero-position indicator 206, the details of which are discussed in U.S. Pat. No. 11,432,999.

The second device 250 comprises a second base 258, a second charging port 260, a second lid 252, a second zero position indicator 256, a second screen 254, a second aperture A2, and a second removable carousel 262 (shown in FIG. 6B). Like with system 100 described above, the second removable carousel 262 comprises a plurality of compartments and is configured to mechanically engage with the second base 258. A user may assemble second device 250 by placing second removable carousel 262 into the second base 258, and then install the second screen 254 and the second lid 252. In some examples, the second device 250 does not include a screen 254. The second lid 202 is configured to mechanically engage with the second base 258, and the second lid 252 defines second aperture A2. When assembled, the second removable carousel 262 is arranged between the second base 258 and the second lid 252 when the second base 258 and the second lid 252 are mechanically engaged.

The second removable carousel 262 comprises a plurality of compartments 262A. 262B, etc. Second removable carousel 262 may also include second gaps 269 between the walls of each compartment and the center of the second removable carousel 262, and second gap ends 269E on the zero-position indicator 256, the details of which are discussed in U.S. Pat. No. 11,432,999.

In some examples, the second device 250 comprises a second authentication device on the second removable carousel 262. In other examples, the second device 250 does not comprise a second authentication device, and both the first device 240 and the second device 250 communicate with the processor 702 of the first device 240 using the first authentication device. In some examples, the processor 702 for the first device 240 communicates with the second device 250 using Bluetooth.

In some examples, the first authentication device and the second authentication device comprise an RFID tag, and ultrawide band (UWB) device, a Bluetooth device, NFC tag, or combinations thereof. In some examples the first device 240 and the second device 250 further include mechanical authentication mechanisms. The mechanical authentication mechanisms may comprise a lock-and-key mechanism, a snap-fit fastener, magnets, screw-in mechanism, or combinations thereof.

In some examples, a second device 250 includes all of the same features as the first device 240, such as a processor 702 and a second authentication device. In other examples, the second device 250 may act as a "dummy" device that relies on the programming of the first device 240 to function (e.g., the second device 250 does not function independently of the first device 240). A single processor 702 in the first device 240 may control both the first device 240 and the second device 250. The processor 702 can instruct the first device 240 and the second device 250 to operate in the same operating mode or a different operating mode.

For example, the screen 204 on the first device 240 may display a user interface with numerous features a user can select. In some examples, the screen may present a user with an option to select how many compartments are in each of the first removable carousel 212 and the second removable carousel 262 to be used with medication dispensing system 200. FIG. 5 depicts an example screen where a user can turn a 7-compartment (or 7-slot) mode on, meaning that a first removable carousel 212, a second removable carousel 262 or both, with seven compartments will be used with medication dispensing system 200. The screen 204 may also include a similar user interface with a 14-compartment mode, meaning that a first removable carousel 212, a second removable carousel 262 or both, with 14 compartments will be used with medication dispensing system 200, or a 21-compartment mode, meaning that a first removable carousel 212, a second removable carousel 262 or both, with 21 compartments will be used with medication dispensing system 200, and so forth. A single medication dispensing system 200 may include options for a 7-compartment mode, a 14-compartment mode, a 21-compartment mode, and a 28-compartment mode, and combinations thereof. In some examples, a medication dispensing system 200 may include operating modes for any number of compartments 1 to 40 (e.g., a 1-compartment operating mode, a 2-compartment operating mode, a 3-compartment operating mode, a 5-compartment operating mode, a 15-compartment operating mode, a 40-compartment operating mode). In some examples, the processor 702 comprises operating modes selected from the group consisting of a 7-compartment mode, a 14-compartment mode, a 21-compartment mode, and a 28-compartment mode.

In some examples of system 200, the processor 702 may select one operating mode for the first device 240 and another operating mode for the second device 250. In some examples, the operating modes are the same. In other examples, the operating modes are different. For example, the first device 240 and the second device 250 may be both set to a 7-compartment mode, a 14-compartment mode, a 21-compartment mode, or a 28-compartment mode. Or, for example, the first device 240 may be set to a 14-compartment mode, and the second device 250 may be set to a 7-compartment mode. All possible combinations of modes for the first device 240 and the second device 250 are contemplated (e.g., one device being set to a 7-compartment mode and the other being set to a 14-compartment mode: one device being set to a 21-compartment mode and the other being set to a 14 compartment mode: one device being set to a 7-compartment mode and the other being set to a 21-compartment mode: one device being set to a 7-compartment mode and the other being set to a 28-compartment mode: one device being set to a 14-compartment mode and the other being set to a 28-compartment mode; and one device being set to a 21-compartment mode and the other being set to a 28-compartment mode.

In some examples, the processor 702 selects a mode for the first device 240 that corresponds to the number of the plurality of compartments in the first removable carousel 212, and the processor 702 selects a mode that corresponds to the number of the plurality of compartments in the second removable carousel 262. For example, a first device 240 may have a first removable carousel with 14 compartments and an electronic authentication device that stores information that the first removable carousel has 14 compartments, and a second device 250 may have a second removable carousel 262 with 7 compartments, and the electronic authentication device of the first device 240 stores information that the second removable carousel has 7 compartments.

As discussed above, the processor 702 and the first electronic authentication device (and second electronic authentication device) can also store patient identifying information such as name, date of birth, Medicaid or Medicare number, or other information traditionally known at Protected Health Information (PHI). Both the processor 702 and the electronics authentication devices store information about the patient using the system 200. In some examples, the first electronic authentication device on the first removable carousel 212 stores information about the number of the plurality of compartments, a patient using the system, or combinations thereof. This information can be used to ensure a match between the information in the processor 702 and the information in an electronic authentication device. In some examples that include a second electronic authentication device, the second electronic authentication device on the second removable carousel 262 stores information about the number of the plurality of compartments, a patient using the system, or combinations thereof.

If the information in the electronic authentication device does not match the information in the processor 702, the system 200 will not dispense medication. If any of the information in the electronic authentication device does not match the information stored by the processor 702, the processor 702 will display an error message on the screen 204 of the first device 204. In examples where the second device 250 also includes a screen 254, the processor 702 of the first device 240 will also display an error message on the screen 254 of the second device 250. This communication can occur using a Bluetooth device that connects the first device 240 and the second device 250.

A mismatch in information can include a mismatch between patient identifying information or the number of the plurality of compartments. In some examples, if there is a mismatch, the processor 702 will send a message to a healthcare provider that there is a mismatch between the information stored in the electronic authentication device and the information stored in the processor 702.

Another aspect of the disclosure is a method for using the systems 100 or 200. A user may take a system 100 that is currently assembled and separate the base 108 from the lid 102, and remove the removable carousel 112 from the base 108. The user may then fill the removable carousel 112 with medication according to the user's medication regimen. The removable carousel 112 may be filled by a patient or a healthcare professional, such as a doctor or an aid in a nursing home. The removable carousel is filled according to a patient's specific medication regimen. Additional details regarding filling the removable carousel are discussed in U.S. Pat. No. 11,432,999. After filling the removable carousel 112, the removable carousel 112 is mechanically engaged with the base 108. As described above, if the mechanical locking authentication features of the base 108 and the removable carousel 112 do not match, the removable carousel 112 and the base 108 will not mechanically engage. The mechanical locking authentication features described above apply to the method of using the system 100. The user then mechanically engages the lid 102 of the system 100 and lines up the aperture A with the zero position indicator 106. The system 100 is then ready to be used.

A user may then program the system 100 to dispense medication according to the patient's medication regimen. The programming may comprise selecting an operating mode, such as a 7-compartment mode, a 14-compartment mode, a 21-compartment mode, or a 28-compartment mode. The details discussed above relative to the operating modes apply to using the system 100. The programming may be done using the screen 104 of the system 100, or by programming remotely using a computer program or mobile application. When a user selects an operating mode, the system will dispense medication according to the operating mode. For example, if the operating mode is a 7-compartment mode to dispense once daily, the system 100 is programmed to dispense medication once daily for 1 week until the compartments are empty.

The user may also program the system 100 to store patient identifying information. As described above, this can include name, date of birth, Medicaid or Medicare number, or other information traditionally known at Protected Health Information (PHI). In some examples, a user only needs to program the system 100 at the first use of the system 100 to include the patient identifying information. In some examples, the user may also program the medication regimen. For example, a user may program that the patient takes four pills, twice daily each, and will use a 14-compartment tray. The system 100 is programmed with the patient's medication regimen and will dispense medication according to that regimen and the operating mode selected. In some examples, this programming is performed remotely by a healthcare professional.

Before medication is dispensed, if the system 100 uses an electronic authentication device, the processor 702 communicates with the electronic authentication device on the removable carousel 112 to check if the information in the electronic authentication device matches the information that has been programmed into the system 100 by the processor 702. For example, the processor 702 checks if the patient identifying information matches the removable carousel 112 and if the operating mode matches the number of the plurality of compartments in the removable carousel 112 that is stored in the electronic authentication device. If all of the information matches, the system 100 will dispense medication according to the patient's medication regimen. Additional details regarding the dispensing are discussed in U.S. Pat. No. 11,432,999.

In some examples, a method is disclosed for dispensing medication from system 200 that has two or more devices. In some examples, a system 200 has two devices, a first device 240 and a second device 250. The description above for the method of dispensing medication from system 100 applies to the dispensing of medication for system 200. For the sake of brevity, not all details are presented here, but the same or similar steps apply.

A user may take a first device 240 and a second device 250 that are currently assembled and separate the first and second bases 208, 258 from the first and second lids 202, 252. Then, the user may remove the first and second removable carousels 212, 262 from the first and second bases 208, 258. The user may then fill the first and second removable carousels 212, 262 with medication according to the user's medication regimen. The first and second removable carousels 212, 262 may be filled by a patient or a healthcare professional, such as a doctor or an aid in a nursing home. The removable carousel is filled according to a patient's specific medication regimen. In a system 200 with two or more devices, the first and second removable carousels 212, 262 can be filled in any suitable arrangement. For example, the first removable carousel 212 may be filled with medication for Monday through Thursday of a week, and a second removable carousel 262 may be filled with medication for Friday through Sunday of a week. Alternatively, the first removable carousel 212 may be filled with 1 week of medication, and a second removable carousel 262 may be filled with a different 1 week of medication. Alternatively the first removable carousel 212 may be filled with medication to be taken in the morning for 1 week, and the second removable carousel 262 may be filled with medication to be taken in the evening for 1 week. Any possible permutation of medication regimen is contemplated.

After filling the first and second removable carousels 212, 262, the first and second removable carousels 212, 262 are mechanically engaged with the respective first and second bases 208, 258. As described above, if the mechanical locking authentication features of the first base 208 and the first removable carousel 212 do not match, or the mechanical locking authentication features of the second base 258 and the second removable carousel 262 do not match, the first and second removable carousels 212, 262 and the first and second bases 208, 258 will not mechanically engage. The mechanical locking authentication features described above apply to the method of using the system 200 and both devices 240, 250. The user then mechanically engages the first lid 202 of the system 200 to the first base 208 and lines up the aperture A1 with the first zero position indicator 206, and the second lid 252 is mechanically engaged to the second base 258 and the second aperture A2 is lined up with the second zero position indicator A2. The system 200 is then ready to be used. Any number of devices can be used with system 200, and each device may be filled with medication in a similar fashion.

A user may then program the system 200 to dispense medication according to the patient's medication regimen. The programming may comprise selecting an operating mode, such as a 7-compartment mode, a 14-compartment mode, a 21-compartment mode, or a 28-compartment mode for each device 240, 250. The details discussed above relative to the operating modes apply to using the system 200. The programming may be done using the first screen 204 on the first device, the second screen 254 on the second device, or by programming remotely using a computer program or mobile application. When a user selects an operating mode, the system will dispense medication according to the operating mode. For example, if first device 240 is programmed with a 7-compartment operating mode to dispense once daily, the first device 240 is programmed to dispense medication once daily for 1 week until the compartments are empty.

The user may also program the each device 240, 250 in system 200 to store patient identifying information. As described above, this can include name, date of birth, Medicaid or Medicare number, or other information traditionally known at Protected Health Information (PHI). In some examples, a user only needs to program the system 200 at the first use of the system 200 to include the patient identifying information. In some examples, the user may also program the medication regimen. For example, a user may program that the patient takes 4 pills in the morning, 4 pills at lunch time, and 4 pills in the evening. The user may program that a first device 240 will use a 14-compartment tray with 4 pills in each compartment, the first device will dispense 4 pills in the morning and 4 pills at lunch time for 1 week. The user may program the second device 250 with a 7 compartment tray with 4 pills in each compartment to dispense 4 pills in the evening for 1 week. Such programming may be beneficial for patients taking large quantities of medication, especially if the pills are large and cannot fit in a single device. Additionally, a patient might wish to carry around two smaller devices rather than one large device based on their lifestyle. The system 200 is programmed with the patient's medication regimen and will dispense medication according to the programmed regimen and the operating mode selected. In some examples, this programming is performed remotely by a healthcare professional.

Before medication is dispensed, if the system 200 uses an electronic authentication device, the processor 702 communicates with the electronic authentication device on the first and second removable carousels 212, 262 to check if the information in the first electronic authentication device (and if used, the second authentication device) matches the information that has been programmed into the system 200 by the processor 702. For example, the processor 702 checks if the patient identifying information matches the first and second removable carousels 212, 262 and if the operating mode matches the number of the plurality of compartments in each of the first and second removable carousels 212, 262 that is stored in the first and second electronic authentication devices. If all of the information matches, the system 200 will dispense medication according to the patient's medication regimen. Additional details regarding the dispensing are discussed in U.S. Pat. No. 11,432,999.

Figure 7:
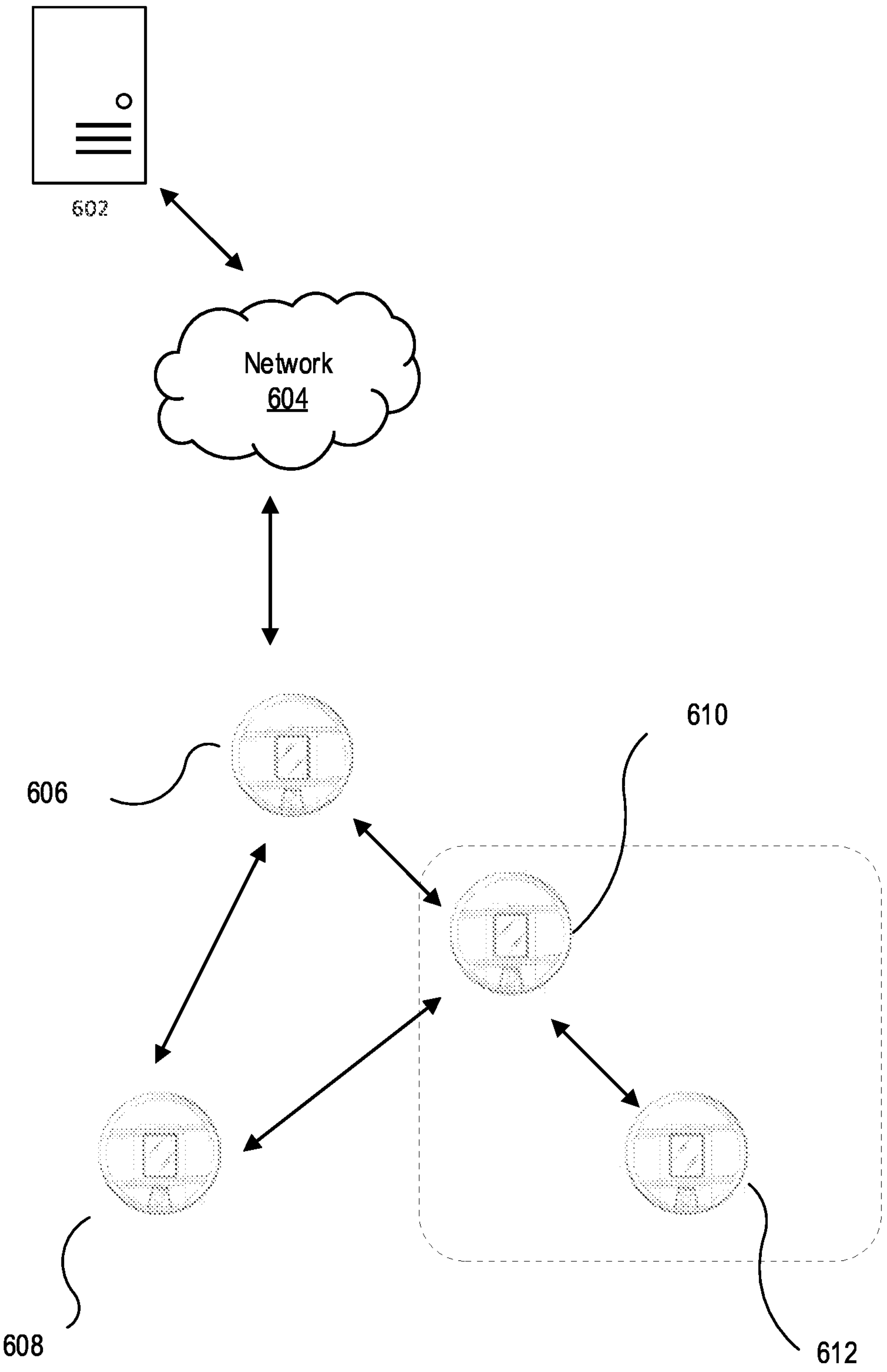
FIG. 7 shows a set of devices arranged in a network.

FIG. 7 is a simplified schematic of a set of dispensing devices according to an embodiment. In FIG. 7, a server 602 is communicatively coupled to a network 604. Network 604 can in turn be coupled to any number of remote network locations, such as hospitals, care nursing homes, houses, apartments, pharmacies, or clinics. In the embodiment shown in FIG. 7, network 604 is shown as being connected to one device 606.

Device 606 is like the devices described above with respect to FIGS. 1-5. Additionally, device 606 that is connected to network 604 is configured to be a part of a mesh network. Additional devices 608, 610, and 612 are also configured to interact in the mesh network, indicated by arrows in FIG. 7.

In a mesh network, devices (e.g., 606-612) can wirelessly interact with one another from a distance. Network traffic is routed from one device to another throughout the network as indicated by the arrows in FIG. 7. As devices go in or out of range of one another, they can connect, disconnect, or reconnect to any other member of the network to send and receive instructions and information.

One beneficial aspect of a mesh network of devices is that only one device (e.g., device 606) need have a screen, or be able to receive commands to adjust settings or features. Other devices throughout the network can be relatively less sophisticated, and can take instructions from a main device (e.g., device 606) or from a computer (not shown) on the network. In this way, the cost and complexity of the additional devices 608-612 can be reduced.

In one example, three individuals live in the same house, each of whom uses some number of devices. A first patient uses device 606, a second patient uses second device 608, and a third patient uses two devices 610 and 612, shown together in a dashed box.

In this scenario, the medication dispensing schedules and communications to and from network 604 can all be carried out by a device 606. The other devices 608-612 receive any instructions, and report medication adherence, back to server 602 via network 604 through the first device 606.

Mesh networks are just one example of a system for data transfer between various devices 606-612. In other embodiments, the devices 606-612 could be connected to one another through a WiFi network, Bluetooth connection, Zigbee, wired connections, NFC connections, or any other wired or wireless communications protocol.

Figure 8:
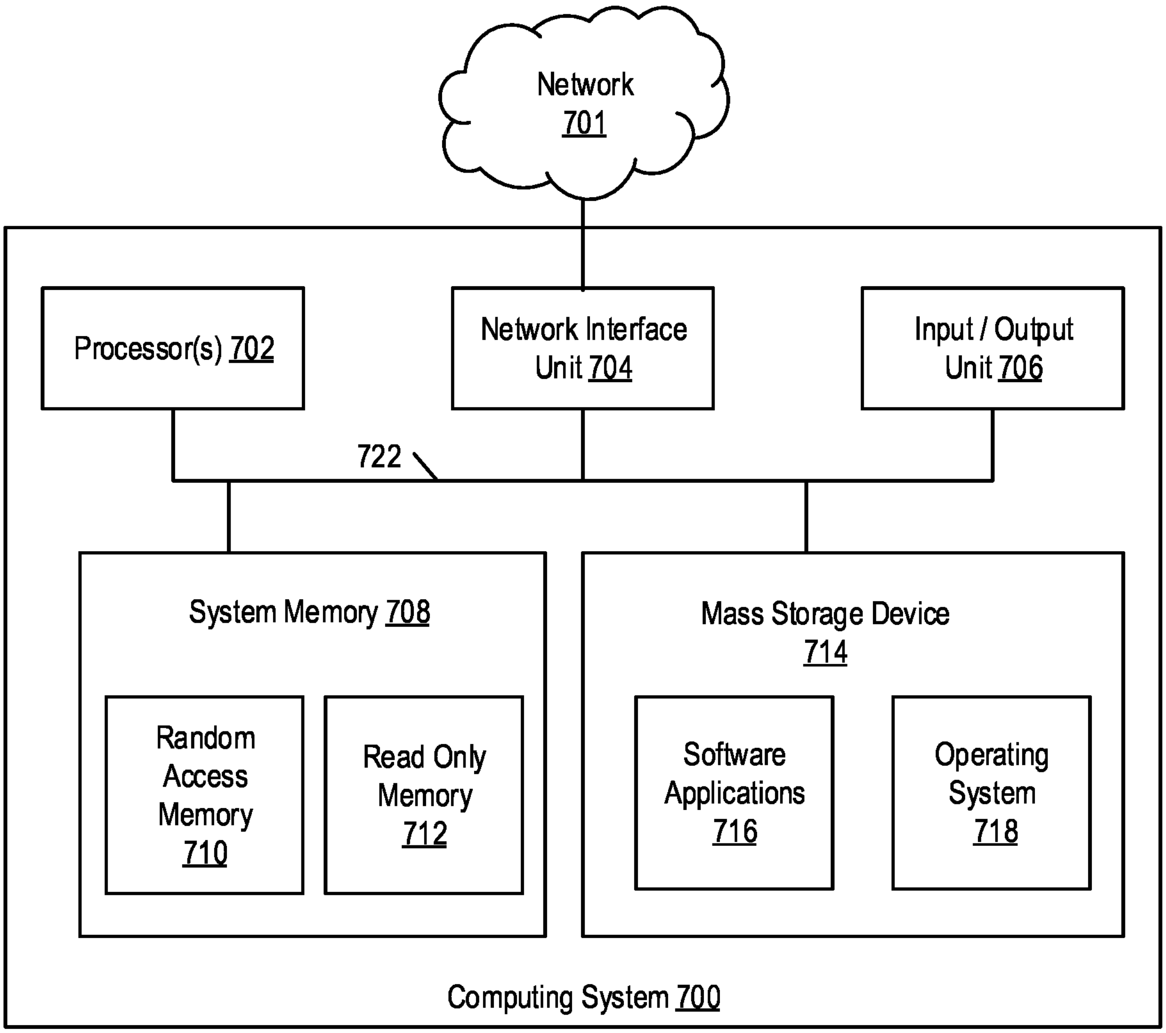
FIG. 8 illustrates an example computing system with which aspects of the present disclosure may be implemented.

FIG. 8 illustrates an example block diagram of a virtual or physical computing system 700 associated with the processor 702 of system 100 and the first device 240 and second device 250 of system 200. The systems 100, 200 described above use a processor 702 to store information and direct the systems 100, 200 to dispense medication in accordance with operating modes and patient information discussed above. One or more aspects of the computing system 700 can be used to implement the processes described herein.

In the embodiment shown, the computing system 700 includes one or more processor 702_s_, a system memory 708, and a system bus 722 that couples the system memory 708 to the one or more processor 702_s_. The system memory 708 includes RAM (Random Access Memory) 710 and ROM (Read-Only Memory) 712. A basic input/output system that contains the basic routines that help to transfer information between elements within the computing system 700, such as during startup, is stored in the ROM 712. The computing system 700 further includes a mass storage device 714, corresponding to the non-volatile memory as described elsewhere in the application. The mass storage device 714 is able to store software instructions and data. The one or more processor 702*s* can be one or more central processing units or other processor 702*s*.

The mass storage device 714 is connected to the one or more processor 702*s* through a mass storage controller (not shown) connected to the system bus 722. The mass storage device 714 and its associated computer-readable data storage media provide non-volatile, non-transitory storage for the computing system 700. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, DVD (Digital Versatile Discs), other optical storage media, magnetic cassettes, magnetic tape, magnetic disk storage or other magnetic storage devices, or any other medium which can be used to store the desired information and which can be accessed by the computing system 700.

According to various embodiments of the invention, the computing system 700 may operate in a networked environment using logical connections to remote network devices through the network 701. The network 701 is a computer network, such as an enterprise intranet and/or the Internet. The network 701 can include a LAN, a Wide Area Network (WAN), the Internet, wireless transmission mediums, wired transmission mediums, other networks, and combinations thereof. The computing system 700 may connect to the network 701 through a network interface unit 704 connected to the system bus 722. It should be appreciated that the network interface unit 704 may also be utilized to connect to other types of networks and remote computing systems. The computing system 700 also includes an input/output controller 706 for receiving and processing input from a number of other devices, including a touch user interface display screen, or another type of input device. Similarly, the input/output controller 706 may provide output to a touch user interface display screen or other type of output device.

The mass storage device 714 and the RAM 710 of the computing system 700 can store software instructions and data. The software instructions include an operating system 718 suitable for controlling the operation of the computing system 700. The mass storage device 714 and/or the RAM 710 also store software instructions, that when executed by the one or more processor 702*s*, cause one or more of the systems, devices, or components described herein to provide functionality described herein. For example, the mass storage device 714 and/or the RAM 710 can store software instructions that, when executed by the one or more processor 702*s*, cause the computing system 700 to receive and execute managing network access control and build system processes.

While particular uses of the technology have been illustrated and discussed above, the disclosed technology can be used with a variety of data structures and processes in accordance with many examples of the technology. The above discussion is not meant to suggest that the disclosed technology is only suitable for implementation with the data structures shown and described above. For examples, while certain technologies described herein were primarily described in the context of queueing structures, technologies disclosed herein are applicable to data structures generally.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., operations, memory arrangements, etc.) described with respect to FIG. 8 are not intended to limit the technology to the particular aspects described. Accordingly, additional configurations can be used to practice the technology herein and/or some aspects described can be excluded without departing from the methods and systems disclosed herein.

Similarly, where operations of a process are disclosed, those operations are described for purposes of illustrating the present technology and are not intended to limit the disclosure to a particular sequence of operations. For example, the operations can be performed in differing order, two or more operations can be performed concurrently, additional operations can be performed, and disclosed operations can be excluded without departing from the present disclosure. Further, each operation can be accomplished via one or more sub-operations. The disclosed processes can be repeated.

Having described the preferred aspects and implementations of the present disclosure, modifications and equivalents of the disclosed concepts may readily occur to one skilled in the art. However, it is intended that such modifications and equivalents be included within the scope of the claims which are appended hereto.

What is claimed is:

1. A system for dispensing medication comprising:

a base having a locking authentication feature and a motor;

a removable carousel comprising a plurality of compartments and a corresponding locking authentication feature; and a processor configured to operate the system based upon a match between the locking authentication feature of the base and the corresponding locking authentication feature of the removable carousel, wherein the removable carousel is configured to mechanically engage with the motor when the locking authentication feature of the base and the corresponding locking authentication feature of the removable carousel match one another, the locking authentication feature of the base and the corresponding locking authentication feature of the removable carousel engaging if the number of the plurality of compartments in the removable carousel matches an operating mode selected by the processor, and wherein the removable carousel mechanically engages with the motor via a receiver that extends from the motor and includes the locking authentication feature.

2. The system of claim 1, wherein the locking authentication feature of the base and the corresponding locking authentication feature of the removable carousel comprise a lock-and-key mechanism, a snap-fit fastener, magnets, or a screw-in mechanism.

3. The system of claim 1, wherein if the locking authentication feature of the base and the corresponding locking authentication feature of the removable carousel do not match one another, the base and the removable carousel will not mechanically engage with each other.

4. The system of claim 1, further comprising a lid configured to mechanically engage with the base, the lid defining an aperture.

5. The system of claim 4, wherein the removable carousel is configured to be arranged between the base and the lid when the base and the lid are mechanically engaged.

6. A system for dispensing medication comprising:

a base;

a removable carousel comprising a plurality of compartments and an electronic authentication device;

wherein the removable carousel is configured to mechanically engage with the base; and a processor configured to operate the system based upon information stored in the electronic authentication device, the processor further comprising operating modes selected from the group consisting of a 7-compartment mode, a 14-compartment mode, a 21-compartment mode, and a 28-compartment mode, wherein the electronic authentication device of the removable carousel stores information about the number of the plurality of compartments, a patient using the system, or combinations thereof, and wherein if the information in the electronic authentication device for the number of the plurality of compartments does not match the operating mode selected by the processor, the system will not dispense medication.

7. The system of claim 6, wherein the processor stores information about the patient using the system.

8. The system of claim 7, wherein if the information in the electronic authentication device for the patient does not match the information about the patient stored by the processor, the system will not dispense medication.

9. The system of claim 8, wherein the processor displays an error message on a screen of the system.

10. The system of claim 9, wherein the processor sends a message to a healthcare provider that there is a mismatch between the information stored in the electronic authentication device and the information stored in the processor.

11. The system of claim 6, wherein when the base and the removable carousel are mechanically engaged, the information stored in the electronic authentication device of the removable carousel directs the processor to select an operating mode corresponding to the information stored in the electronic authentication device.

12. The system of claim 6, wherein the electronic authentication device comprises an RFID tag, an ultrawide band (UWB) device, a Bluetooth device, or an NFC tag.

13. The system of claim 6, further comprising a lid configured to mechanically engage with the base, the lid defining an aperture.

14. The system of claim 13, wherein the carousel is configured to be arranged between the base and the lid when the base and the lid are mechanically engaged.

* * * * *